(12) United States Patent
Rabiner

(10) Patent No.: US 6,325,065 B1
(45) Date of Patent: Dec. 4, 2001

(54) CERVICAL FITTING

(75) Inventor: Robert A. Rabiner, North Reading, MA (US)

(73) Assignee: Omnisonics Medical Technologies, Inc., Wilmington, MA (US)

(*) Notice: Subject to any disclaimer, the term of this patent is extended or adjusted under 35 U.S.C. 154(b) by 0 days.

(21) Appl. No.: 09/620,160

(22) Filed: Jul. 20, 2000

Related U.S. Application Data

(60) Provisional application No. 60/163,051, filed on Nov. 2, 1999.

(51) Int. Cl.$^7$ .................................................. A61F 6/06
(52) U.S. Cl. ............................................ 128/830; 606/193
(58) Field of Search ............................ 128/830, 831, 128/832, 840, 841; 604/55, 117, 164–171

(56) References Cited

U.S. PATENT DOCUMENTS

| | | | |
|---|---|---|---|
| 4,480,642 | * 11/1984 | Stoy | 606/193 |
| 4,877,037 | * 10/1989 | Ko | 604/117 |
| 5,464,409 | * 11/1995 | Mohajer | 604/170.03 |
| 5,961,444 | 10/1999 | Thompson | 600/33 |
| 6,113,580 | * 9/2000 | Dolis | 604/181 |

\* cited by examiner

*Primary Examiner*—Michael A. Brown
(74) *Attorney, Agent, or Firm*—Kenyon & Kenyon

(57) ABSTRACT

A one-piece cervical fitting has a passage formed therethrough which receives an elongated medical device such as an endoscope. The passage forms a fluid-tight seal with the outer surface of the medical device. The outer surface of the fitting defines a pilot portion which is of reduced outer dimension to facilitate entry of the fitting into the cervical canal of a human uterus. The pilot portion joins a tapered outer surface portion which enables the fitting to form a fluid-tight seal with uteri of different sizes. The tapered portion joins with an outer surface portion of constant outer dimension which in turn joins with an enlarged end portion.

4 Claims, 2 Drawing Sheets

CERVICAL FITTING

This application claims benefit of provisional application Ser. No. 60/163,051 filed Nov. 2, 1999.

BACKGROUND OF THE INVENTION

The present invention relates to a cervical fitting for use with a medical device such as an endoscope or a hysteroscope. In the performance of hysteroscopy, for example, a doctor may insufflate a human uterus with a suitable fluid such as a saline liquid media to cause distension of the walls of the uterus. This causes the walls to separate to allow a visual inspection of the endometrial lining. The fluid is sometimes continually introduced into the uterus so as to maintain a clear field of view. The fluid is introduced into the uterus via the cervical canal using a catheter, scope or sheath and the like.

The problem which commonly arises during such procedures is that the fluid introduced into the uterus leaks from the uterus and thereby causes the distension of the walls of the uterus to be reduced which prevents satisfactory viewing of the endometrial lining. Furthermore, fluid may accumulate on the floor of the examining or operating room. This leakage is generally caused by the axial and rocking motion of the medical devices within the cervical canal.

SUMMARY OF THE INVENTION

The cervical fitting invention is designed to be used in combination with small diameter endoscopes or hysteroscopes to provide a simple and effective means to prevent leakage during medical procedures, thereby maintaining distension of the walls of a human uterus. The fitting has a passage which extends therethrough and which receives an associated medical device so that a substantially fluid-tight seal is formed between the passage and the outer surface of the medical device.

The cervical fitting has a tapered outer surface portion which fits within the cervical canal and because of its tapered configuration is adapted to form a substantially fluid-tight seal with the surface of the cervical canal in uteri of different sizes. The fitting minimizes movement in the cervical canal since the rocking movement occurs only at a particular part of the tapered outer surface portion of the fitting.

The fitting also includes a pilot outer surface portion of reduced dimension which is disposed at the reduced end of the tapered outer surface portion. The pilot portion facilitates initial entry of the fitting into the cervical canal. An outer surface portion of substantially constant outer dimension is disposed at the large end of the tapered outer surface portion and joins with an enlarged end portion.

The outer shape of the cervical fitting is designed to be atraumatic and allows easy placement of the fitting and medical device in place within a cervical canal. The fitting effectively holds the medical device in place once the fitting is positioned within a cervical canal. The most important feature of the fitting is that lateral or rocking motion of the medical device does not cause leakage from the uterus since the fitting fills the cervical canal and continues to provide a substantially fluid-tight seal with the surface of the canal at all times during use.

The fitting allows the medical device to be adjusted into many different positions as required while preventing leakage. The fitting is comfortable to a patient and can be used with small instruments other than those discussed above. An additional advantage of the invention that it is relatively cheap to manufacture; and therefore the fitting may be disposed of after a single use.

DESCRIPTION OF THE PREFERRED EMBODIMENT

Figure 1:
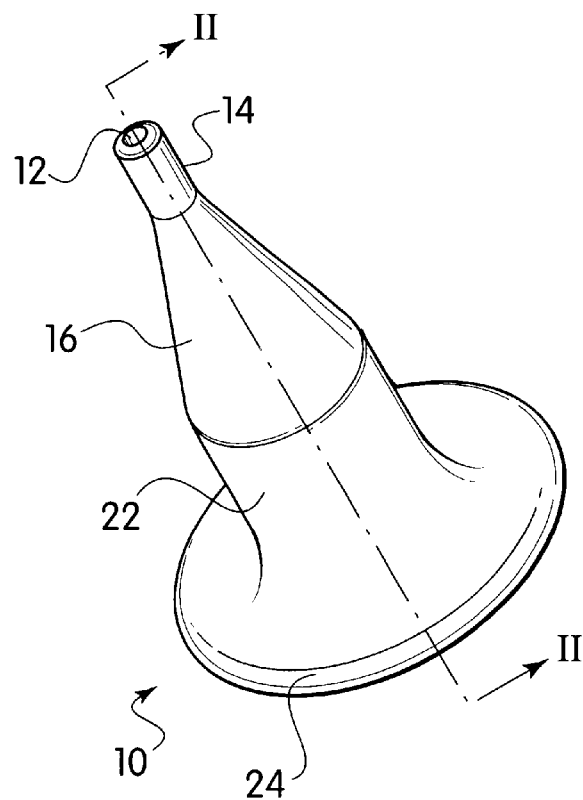
FIG. 1 is a top perspective view of the cervical fitting.
Figure 2:
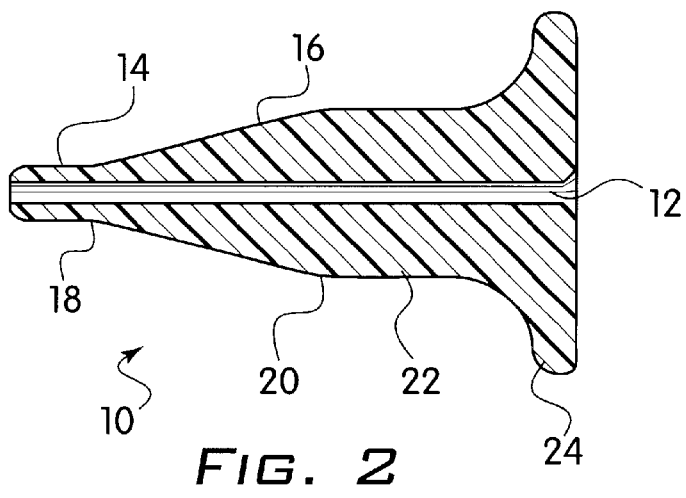
FIG. 2 is a sectional view taken on line 2—2 of FIG. 1.

Referring now to the drawing wherein like reference characters designate corresponding parts throughout the several views, as seen in FIGS. 1 and 2, the cervical fitting 10 is a one-piece body formed of a suitable plastic material such as DELRIN having non-toxic qualities suitable for use with a human uterus. The fitting has a central passage 12 extending axially of the fitting from one end to the other. As seen in FIG. 2, the outer surface at the left-hand end of the fitting defines a pilot portion 14 of circular cross-section which is of less outer dimension or diameter than than the remainder of the outer surface of the fitting. As seen in FIG. 2, the outer surface at the left-hand end of the fitting defines a pilot portion 14 of circular cross-section which is of less outer dimension or diameter than than the remainder of the outer surface of the fitting.

Pilot portion 14 joins with a tapered outer surface portion 16 of frusto-conical configuration which tapers from a minimum diameter at point 18 to a maximum diameter at point 20. The tapered portion joins with an outer surface portion 22 which has a substantially constant outer dimension or diameter. Outer surface portion 22 joins with an enlarged end portion 24.

Figure 3:
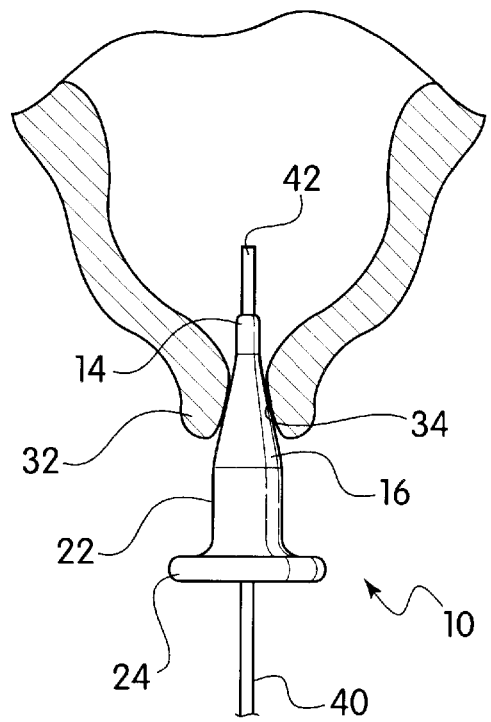
FIG. 3 is a view showing the fitting disposed within the cervical canal of a uterus with a medical device supported therein.

Referring to FIG. 3, a human uterus includes a cervix 32 having a cervical canal 34 therein. A fitting 10 is shown in operative position within the cervical canal to provide a substantially fluid-tight seal with the surface of the canal. A medical device such as an endoscope is illustrated as having its conventional sheath 40 extending through the channel within the fitting with the terminal end 42 of the medical device disposed within the uterus.

Figure 4:
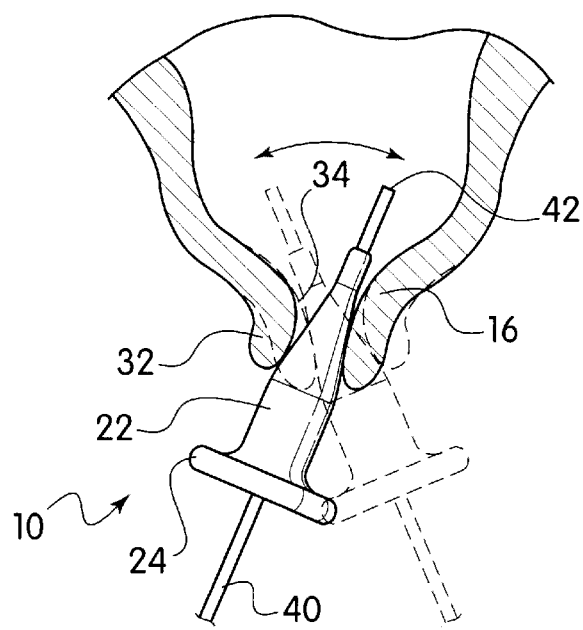
FIG. 4 shows the manner in which the fitting and an associated medical device may be moved with respect to the uterus while preventing leakage of fluid from the uterus.

Referring to FIG. 4, the fitting and the medical device associated therewith are shown in solid lines and broken lines at two different extreme angular positions, it being understood that the fitting may be moved into any intermediate position between these extreme positions when desired. Therefore, the fitting and medical device may be rocked into various relationships relative to the uterus while maintaining a substantially fluid-tight seal with the surface of the cervical canal as shown.

It is noted, that the medical device can also be moved axially through the channel in the fitting as required to view different areas of the interior of the uterus while maintaining an effective seal between the inner surface of passage 12 and the outer surface of the medical device. This is possible since the medical device is snugly but slidably received within the passage in the fitting.

The invention has been described with reference to a preferred embodiment. Obviously, various modifications, alterations and other embodiments will occur to others upon reading and understanding this specification. It is our intention to include all such modifications, alterations and alternate embodiments insofar as they come within the scope of the appended claims or the equivalent.

What is claimed is:

1. In combination, an elongated medical device having an outer surface, a one-piece cervical fitting having a passage formed therethrough, said passage receiving said device and forming a substantially fluid-tight seal with said outer surface, said fitting including a tapered outer surface portion that is adapted to provide a substantially fluid-tight seal with the surface of the cervical canal of human uteri of different sizes, the tapered outer surface portion having a minimum diameter sized to allow entry into the cervical canal and a maximum diameter sized to prevent entrance into the cervical canal.

2. The combination as defined in claim 1 wherein said fitting includes a pilot outer surface portion adjacent said tapered outer surface portion, said pilot outer surface portion being of less outer dimension than said tapered portion to facilitate entry of the fitting into the cervical canal of a human uterus.

3. The combination as defined in claim 2 wherein said fitting includes an outer surface portion having a substantially constant outer dimension and being disposed adjacent said tapered outer surface portion.

4. The combination as defined in claim 1 wherein said fitting has an enlarged end portion spaced from said tapered outer surface portion.

* * * * *